US00PP30438P2

(12) United States Plant Patent
Koppe

(10) Patent No.: US PP30,438 P2
(45) Date of Patent: Apr. 23, 2019

(54) ***BEGONIA* PLANT NAMED 'KRILORW01'**

(50) Latin Name: ***Begonia* x *hiemalis***
Varietal Denomination: KRILORW01

(71) Applicant: Lubbertus H. Koppe, Putten (NL)

(72) Inventor: Lubbertus H. Koppe, Putten (NL)

(73) Assignee: KOPPE ROYALTY B.V., Putten (NL)

( * ) Notice: Subject to any disclaimer, the term of this patent is extended or adjusted under 35 U.S.C. 154(b) by 0 days.

(21) Appl. No.: 15/732,402

(22) Filed: Nov. 6, 2017

(51) Int. Cl.
*A01H 5/02* (2018.01)

(52) U.S. Cl.
USPC ..... Plt./344

(58) Field of Classification Search
USPC ..... Plt./263.1, 343, 344
See application file for complete search history.

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Begonia* plant named 'KRILORW01' characterized by its upright to outwardly spreading and mounded plant habit; moderately vigorous growth habit; freely flowering habit; double type flowers that are red and light green to white in color and held above and beyond the foliar plane; and excellent postproduction longevity.

2 Drawing Sheets

Botanical designation: *Begonia* x *hiemalis*.
Cultivar denomination: 'KRILORW01'.

BACKGROUND OF THE INVENTION

The present invention relates to a new and distinct cultivar of *Begonia* plant, botanically known as *Begonia* x *hiemalis*, commercially referred to as an Elatior *Begonia* and hereinafter referred to by the name 'KRILORW01'.

The new *Begonia* plant is a product of a planned breeding program conducted by the Inventor in Ermelo, The Netherlands. The objective of the breeding program is to create new vigorous *Begonia* plants with excellent postproduction longevity and attractive flower color.

The new *Begonia* plant is a naturally-occurring whole plant mutation of *Begonia* x *hiemalis* 'Polly', not patented. The new *Begonia* plant was discovered and selected by the Inventor as a single flowering plant from within a population of plants of the mutation parent in a controlled greenhouse environment in Ermelo, The Netherlands in May, 2013. Asexual reproduction of the new *Begonia* plant by terminal vegetative cuttings taken in a controlled greenhouse environment in Ermelo, The Netherlands since May, 2014 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'KRILORW01'. These characteristics in combination distinguish 'KRILORW01' as a new and distinct *Begonia* plant:

1. Upright to outwardly spreading and mounded plant habit.
2. Moderately vigorous growth habit.
3. Freely flowering habit.
4. Double type flowers that are red and light green to white in color and held above and beyond the foliar plane.
5. Excellent postproduction longevity.

Plants of the new *Begonia* differ primarily from plants of the mutation parent, 'Polly', in flower type and color as plants of 'Polly' have semi-double flowers that are pink and white in color.

Plants of the new *Begonia* can be compared to plants of *Begonia* x *hiemalis* 'Renate', not patented. In side-by-side comparisons conducted in Ermelo, The Netherlands, plants of the new *Begonia* differ primarily from plants of 'Renate' in flower type and color as plants of 'Renate' have semi-double flowers that are dark pink and yellow to white in color.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical plant of 'KRILORW01' grown in a container.

The photograph on the second sheet are close up views of the upper (right) and lower (left) surfaces of typical leaves and flowers of 'KRILORW01', and in the center of the photograph is a close-up view of typical flower buds.

DETAILED BOTANICAL DESCRIPTION

The aforementioned photographs and following observations and measurements describe plants grown during the late spring and early summer in 12-cm containers in a glass-covered greenhouse in Ermelo, The Netherlands and under cultural practices typical of commercial *Begonia* production. During the production of the plants, day temperatures averaged 20° C. and night temperatures averaged 18° C. Plants were three months old when the photographs and description were taken. In the following description, color references are made to The Royal Horticultural Society Colour Chart, 2015 Edition, except where general terms of ordinary dictionary significance are used.

Botanical classification: *Begonia* x *hiemalis* 'KRILORW01'.

Parentage: Naturally-occurring whole plant mutation of *Begonia* x *hiemalis* 'Polly', not patented.

Propagation:

*Type*.—By terminal vegetative cuttings.

*Time to initiate roots, summer and winter*.—About 20 days at temperatures about 20° C.

*Time to produce a rooted young plant, summer and winter*.—About five weeks at temperatures about 20° C.

*Root description*.—Fine, fibrous; typically white to orange brown in color, actual color of the roots is dependent on substrate composition, water quality, fertilizer type and formulation, substrate temperature and physiological age of roots.

*Rooting habit*.—Freely branching; medium density; plants of the new *Begonia* have not been observed to form tubers.

Plant description:

*Plant habit and form*.—Upright to outwardly spreading and mounded plant habit; overall plant shape, broadly obovate to nearly globular.

*Growth habit*.—Moderately vigorous growth habit and moderate growth rate; suitable for 12-cm and larger containers; under optimal environmental and cultural conditions, usually about twelve weeks are required to produce proportional plants in 12-cm containers.

*Branching habit*.—Moderately freely branching with about four primary branches developing per plant.

*Plant height, soil level to top of foliar plane*.—About 24.1 cm.

*Plant height, soil level to top of floral plane*.—About 28.7 cm.

*Plant width*.—About 32.9 cm.

*Lateral branches*.—Length: About 12.7 cm. Diameter: About 9 mm. Internode length: About 2.9 cm. Strength: Moderately strong. Aspect: About 25° from vertical. Texture and luster: Initially, sparsely pubescent and becoming smooth and glabrous with development; moderately glossy. Color, developing: Close to 146C. Color, developed: Close to 148A to 148B; proximally, closer to 183A.

*Leaves*.—Arrangement: Alternate, simple. Length: About 12.7 cm. Width: About 9.7 cm. Shape: Ovate, asymmetrical. Apex: Acute. Base: Hastate. Margin: Crenate to dentate; undulate. Texture and luster, upper surface: Smooth, glabrous; moderately velvety; slightly glossy. Texture and luster, lower surface: Sparsely pubescent along venation; slightly velvety; slightly glossy. Venation pattern: Laciniate. Color: Developing leaves, upper surface: Darker than between NN137A and 143A. Developing leaves, lower surface: Close to 191A to 191B. Fully expanded leaves, upper surface: Darker than between 139A and 147A; venation, close to 144A. Fully expanded leaves, lower surface: Close to 191A; towards the margins, slightly tinged with close to 181B to 181C; venation, close to 146C. Petioles: Length: About 6.6 cm. Diameter: About 5 mm to 5.5 mm. Strength: Low, flexible. Texture and luster, upper and lower surfaces: Sparsely pubescent; moderately glossy. Color, upper surface: Close to 176A. Color, lower surface: Close to N199C. Stipules: Length: About 1.2 cm. Width: About 1.4 cm. Shape: Roughly deltoid. Apex: Bluntly acute. Base: Broadly cuneate. Margin: Finely ciliate. Texture and luster, upper and lower surfaces: Smooth, glabrous; moderately glossy. Color, upper and lower surfaces: Close to 145A.

Flower description:

*Flower appearance and flowering habit*.—Double type rotate flowers with four tepals and numerous tepaloids; flowers arranged in axillary compound cymes; freely flowering habit with typically about nine flowers per cyme and about 290 flowers and flower buds developing per plant; many cymes in flower simultaneously; flowers positioned above and beyond the foliar plane and face upright to outwardly.

*Natural flowering season*.—Plants begin flowering about six weeks after planting; plants will flower year round regardless of nyctoperiod, however plants flower earlier and more abundantly from spring into the autumn in The Netherlands.

*Postproduction longevity*.—Individual flowers last about ten days on the plant; flowers not persistent; excellent postproduction longevity, plants maintain good substance for about five to six weeks in an interior environment.

*Fragrance*.—None detected.

*Inflorescence height*.—About 12.5 cm.

*Inflorescence diameter*.—About 8.4 cm.

*Flowers*.—Shape: Rotate, fully double type. Diameter: About 4.7 cm. Depth (height): About 1.6 cm.

*Flower buds*.—Length: About 1.8 cm. Diameter: About 0.8 cm to 2.1 cm. Shape: Reniform, flattened. Texture and luster: Glabrous; slightly velvety; matte. Color: Close to between 145D and 154D; towards the margins, close to 46B to 46D.

*Tepals*.—Quantity and arrangement per flower: Usually about four per flower arranged in two whorls. Length, lower tepals: About 2.7 cm. Width, lower tepals: About 3.2 cm. Length, upper tepals: About 2 cm. Width, upper tepals: About 2.2 cm. Shape, all tepals: Reniform to nearly orbicular. Apex, all tepals: Rounded. Base, all tepals: Reniform. Margin, all tepals: Entire; slightly undulate. Texture and luster, upper surface, lower tepals: Smooth, glabrous; moderately velvety; matte. Texture and luster, lower surface, lower tepals: Smooth, glabrous; moderately velvety; slightly glossy. Texture and luster, upper and lower surfaces, upper tepals: Smooth, glabrous; moderately velvety; matte. Color, lower tepals: When opening, upper surface: Close to 45B; fading towards the base to close to 145B. When opening, lower surface: Close to 45D; fading towards the base to close to 145B. Fully opened, upper surface: Close to between 44A and 45B; fading towards the base to close to 145B; venation, similar to lamina color; colors do not change with development. Fully opened, lower surface: Close to 45D; fading towards the base to close to 145B; venation, similar to lamina color; colors do not change with development. Color, upper tepals: When opening, upper surface: Close to 43A; fading towards the base to close to 145B. When opening, lower surface: Close to 45D; fading towards the base to close to 145B. Fully opened, upper surface: Close to 46C; fading towards the base to close to 157D, venation, similar to lamina color; colors do not change with development. Fully opened, lower surface: Close to 46D; fading towards the base to close to 157D; venation, similar to lamina color; colors do not change with development.

*Tepaloids*.—Quantity and arrangement per flower: Typically about 13 per flower clustered at the center of the flower. Length: About 0.7 cm to 1.6 cm. Width: About 0.4 cm to 1.4 cm. Shape: Obovate. Apex: Obtuse. Base: Cuneate. Margin: Entire; slightly undulate. Texture and luster, upper surface: Smooth, glabrous; moderately velvety; matte. Texture and luster, upper surface: Smooth, glabrous; slightly velvety; matte. Color: When opening, upper surface: Close to 150D; towards the margins and apex, close to 45C to 45D. When opening, lower surface: Close to 150D; towards the margins and apex, close to 45B to 45C. Fully opened, upper and lower surfaces: Close to 150D; mid-section, close to 155C; towards the margins and apex, close to 45B to 45C; venation, similar to lamina color; color does not change with development.

*Peduncles*.—Length: About 5.2 cm. Diameter: About 4 mm to 5 mm. Strength: Moderately strong. Aspect: About 40° from lateral branch axis. Texture and luster: Smooth, glabrous; moderately glossy. Color: Close to 144A.

*Pedicels*.—Length: About 2.4 cm. Diameter: About 2 mm. Strength: Moderately strong. Aspect: About 30° from peduncle axis. Texture and luster: Smooth, glabrous; glossy. Color: Close to 145B.

*Flower bracts*.—Quantity per flower: Two. Length: About 1.3 cm. Width: About 1.3 cm. Shape: Broadly ovate. Apex: Obtuse. Base: Broadly cuneate. Margin: Finely ciliate. Texture and luster, upper and lower surfaces: Smooth, glabrous; slightly glossy. Color, upper and lower surfaces: Close to 144B; venation, similar to lamina color.

*Reproductive organs*.—Stamens and pistils: None observed; male and female flower development has not been observed on plants of the new *Begonia* to date; no seed nor fruit production has been observed to date.

Disease & pest resistance: Resistance to pathogens and pests common to *Begonia* plants has not been observed on plants of the new *Begonia* to date.

Temperature tolerance: Plants of the new *Begonia* have been observed to tolerate high temperatures of about 35° C. and to be suitable for USDA Hardiness Zones 10 to 12.

It is claimed:

1. A new and distinct *Begonia* plant named 'KRILORW01' as illustrated and described.

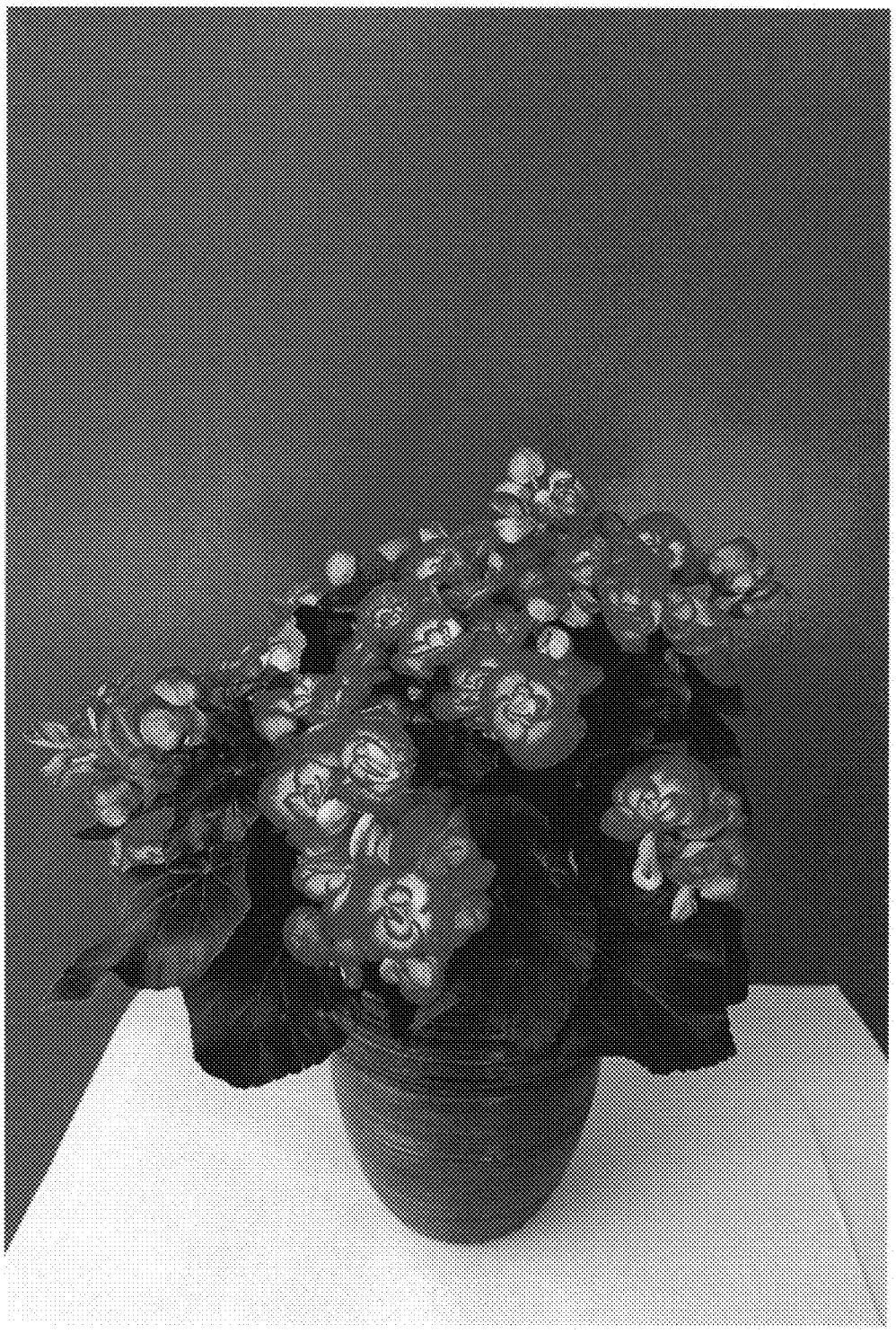

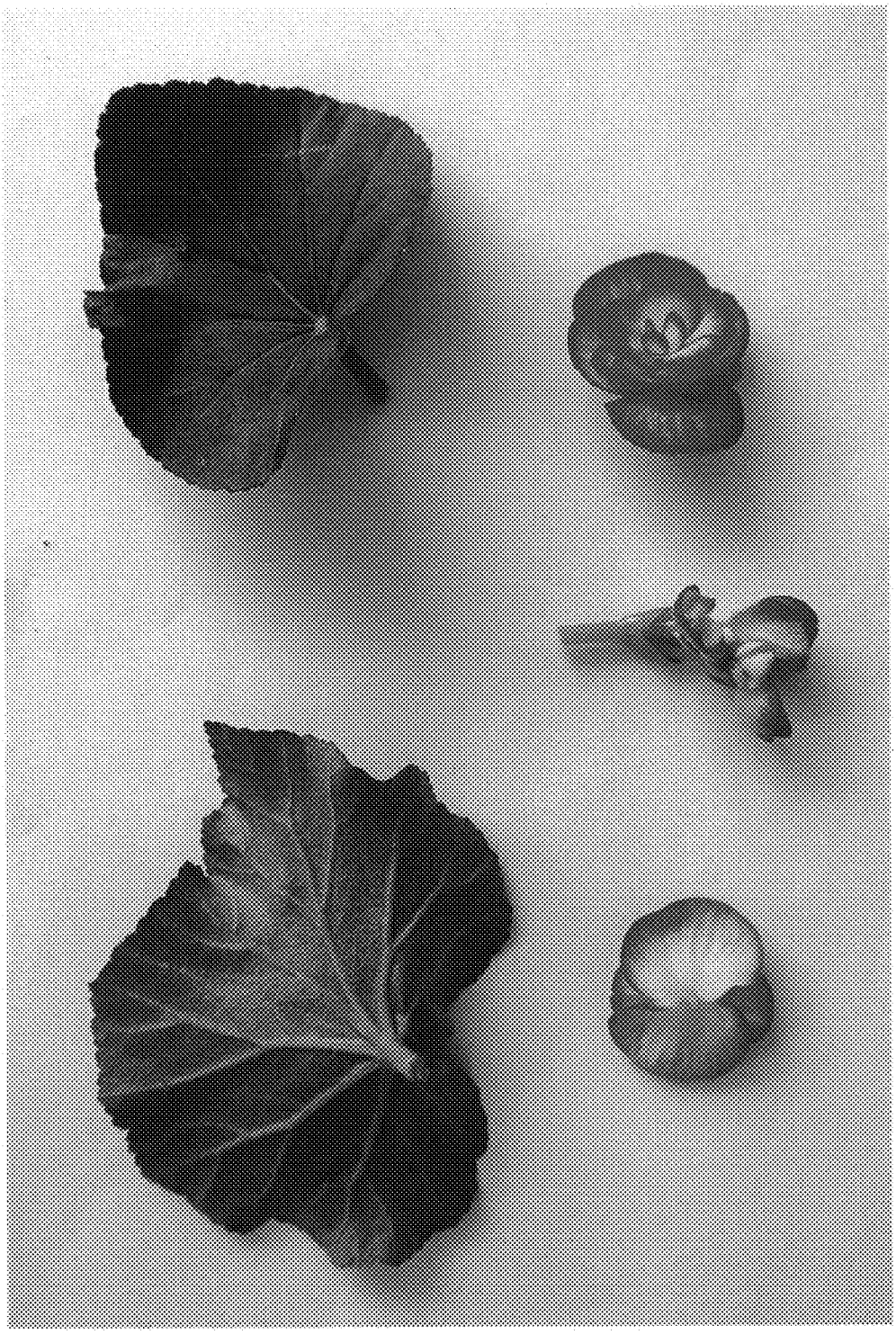

* * * * *